(12) United States Patent
Howard

(10) Patent No.: US 6,569,446 B1
(45) Date of Patent: May 27, 2003

(54) SOLUBILIZATION OF FLAVONOLS

(75) Inventor: Alan N. Howard, Cambridge (GB)

(73) Assignee: The Howard Foundation, Cambridge (GB)

( * ) Notice: Subject to any disclaimer, the term of this patent is extended or adjusted under 35 U.S.C. 154(b) by 0 days.

(21) Appl. No.: 09/504,747

(22) Filed: Feb. 16, 2000

Related U.S. Application Data

(63) Continuation-in-part of application No. 08/978,158, filed on Nov. 25, 1997, now Pat. No. 6,086,910, which is a continuation-in-part of application No. 08/934,055, filed on Sep. 19, 1997, now Pat. No. 6,099,854.

(30) Foreign Application Priority Data

| Sep. 20, 1996 | (GB) | 9617700 |
| May 31, 1997 | (GB) | 9711171 |
| May 31, 1997 | (GB) | 9711172 |
| May 31, 1997 | (GB) | 9711173 |

(51) Int. Cl.$^7$ ............................................. A23K 1/165
(52) U.S. Cl. ................. 424/442; 464/441; 464/443; 464/456; 464/464; 514/456
(58) Field of Search .................... 424/442; 464/441, 464/443, 456, 464; 514/456

(56) References Cited

U.S. PATENT DOCUMENTS

| 4,698,360 A | 10/1987 | Masquelier | 514/456 |
|---|---|---|---|
| 4,808,574 A | 2/1989 | Brekhman | 514/23 |
| 4,857,327 A | 8/1989 | Virdalm | 424/195.1 |
| 4,913,909 A | 4/1990 | Hara | 424/688 |
| 5,141,611 A | 8/1992 | Ford | 204/182.4 |
| 5,352,384 A | 10/1994 | Shen | 252/398 |
| 5,464,619 A | 11/1995 | Kuznicki | 424/195.1 |
| 5,470,589 A | 11/1995 | Shi | 424/698 |
| 5,474,774 A | 12/1995 | Walker | 424/195.1 |
| 5,525,341 A | 6/1996 | Walker | 424/195.1 |
| 5,554,645 A | 9/1996 | Romanczyk | 514/453 |
| 5,587,176 A | 12/1996 | Warren | 424/443 |
| 5,591,771 A | 1/1997 | Markonius | 514/456 |
| 5,607,965 A | 3/1997 | Kondo | 514/456 |
| 5,637,561 A | 6/1997 | Shen | 514/2 |
| 5,650,432 A | 7/1997 | Walker | 514/456 |
| 5,686,082 A | 11/1997 | N'Guyen | 424/401 |
| 5,762,936 A | 6/1998 | Ronzio | 424/195.1 |
| 5,780,060 A | 7/1998 | Levy | 424/489 |
| 5,908,650 A * | 6/1999 | Lenoble et al. | 426/262 |

FOREIGN PATENT DOCUMENTS

| EP | 0 024 731 | 3/1981 |
| EP | 0 169 347 | 1/1986 |
| EP | 0 267 630 | 5/1988 |
| EP | 0 384 796 | 8/1990 |
| EP | 0 692 480 | 1/1996 |
| EP | 0 713 706 | 5/1996 |
| EP | 1 072 265 A1 | 1/2001 |
| FR | 2 577 437 | 2/1985 |
| GB | 1 092 269 | 11/1967 |
| GB | 1 195 050 | 6/1970 |
| GB | 1 235 379 | 6/1971 |
| GB | 1 349 483 | 4/1974 |
| GB | 2 317 561 A | 4/1998 |
| WO | WO 94/22321 | 10/1994 |
| WO | WO 95/13360 | 5/1995 |
| WO | WO 96/13179 | 5/1996 |
| WO | WO 98/11789 | 3/1998 |

OTHER PUBLICATIONS

Scheffeldt et al, Journal of Food Science, 43:517–520, 1978.
Derwent Publications, AN 1980–19056C (XP–002167810).
Derwent Publications, AN 1990–159125 (XP–002167811).
Ziemelis, G., et al., *Precipitation of flavonols in a dry red table wine*, Chemistry and Industry, Dec. 6, 1969, pp. 1781–1782.
Database WPI, AN 95–280915, "New Catechin Glycoside Derivative Phenol Oxidase Inhibit Antioxidant Hypocholesterolaemic Agent Health Food Addivtive", *Derwent Publications Ltd.*, Jul. 18, 1995.
Frankel, E.N., et al., "Principal Phenolic Phytochemicals in Selected California Wines and Their Antioxidant Activity in Inhibiting Oxidation of Human Low–Density Lipoproteins", J. Agric. Food Chem., 1995, 43, 890–894.

* cited by examiner

*Primary Examiner*—Theodore J. Criares
*Assistant Examiner*—Jennifer Kim
(74) *Attorney, Agent, or Firm*—Piper Rudnick LLP; Perry E. Van Over

(57) ABSTRACT

A method of increasing the solubility in water of a flavonol component of a flavonol-containing composition, the method including the steps of providing a flavonol-containing composition, providing an anthocyanin-containing composition and mixing the two compositions.

28 Claims, 4 Drawing Sheets

SOLUBILIZATION OF FLAVONOLS

This Application is a continuation-in-part of U.S. application Ser. No. 08/978,158, filed Nov. 25, 1997, now U.S. Pat. No. 6,086,910, which is a continuation-in-part of U.S. application Ser. No. 08/934,055 filed Sep. 19, 1997, now U.S. Pat. No. 6,099,854.

FIELD OF THE INVENTION

This invention relates to a method of increasing the solubility of flavonols and their related compounds in water and aqueous solutions, and to a method of providing soluble flavonol-containing compositions.

BACKGROUND TO THE INVENTION

Polyphenols are those compounds which comprise more than one phenolic group. Among the polyphenols are the following classes: flavonoids (a term often used to denote polyphenols in general, but more commonly in Europe to denote only the flavones), the flavanols, proanthocyanidins (also called procyanidols, procyanins, procyanidins and tannins) and anthocyanins.

The flavones are compounds with a basic structure shown in FIG. 1 in which two benzene rings (A and B) are linked with a heterocyclic six member ring C containing a carbonyl group. Ring B can be joined in position 2 (as illustrated) to give a flavone or to position 3 to give an iso flavone. Hydroxylation can occur at one or more of positions 3, 5, 7, and 3', 4', 5' to give compounds called flavonols. Typical examples of flavonols are: quercetin (hydroxylated at positions 3, 5, 7, 3', 4'), kaempferol (hydroxylated at positions 3, 5, 7, 4'), and myricetin (hydroxylated at positions 3, 5, 7, 3', 4', 5'). Flavonols can exist naturally as the aglycone or as O-glycosides (e.g. with D-glucose, galactose, arabinose, rhamnose etc). Other forms of substitution such as methylation, sulphation and malonylation are also found.

The flavanols have a basic structure shown in FIG. 2. The two most common flavanols are catechin (hydroxyl groups at positions 5, 7, 3', 4') and its stereo-isomer epi-catechin. The hydroxyl groups can be esterified with gallic acid. The proanthocyanidins are polymers of catechin and/or epicatechin and can contain up to 8 or more repeat units. These compounds are often called proanthocyanidins, procyanidins or tannins.

The anthocyanins are colored substances, sometimes called anthocyanidins. The monomeric anthocyanins have a basic structure as shown in FIG. 3. Typical examples are: cyanidin (hydroxylated at positions 3, 5, 7, 3', 4'), delphinidin (hydroxylated at positions 3, 5, 7, 4', 5') and pelargonidin (hydroxylated at positions 3, 5, 7, 3'). The hydroxyl groups are usually glycosylated and/or methoxylated (e.g. malvidin is substituted at the 3' and 5' hydroxyl groups and paeonidin and petunidin are substituted at the 3' hydroxyl group). In addition polymers of these anthocyanins exist which are classified as polymeric anthocyanins.

Within the general term "polyphenols" are also included the dihydroxy and trihydroxy benzoic acids and the phytoalexins, a typical example of which is resveratrol.

Polyphenols are found in various amounts in large numbers of natural products especially plant material such as fruit and vegetables. A particular rich source is the grape, in which the polyphenols are plentiful in the skins and seeds, but not in the pulp. During the manufacture of grape juice, quantities of polyphenols are expressed into the juice, and the polyphenol content will depend on such factors as the type of grape, the climate in which it is grown, and the manufacturing process used in making the juice. Some grape juice, especially that made from the Concord grape, may contain as much as 2.5 g polyphenol per litre of juice. Grape skins and seeds are commercially extracted with water and other solvents to obtain polyphenols. In addition, polyphenols from grape skins and seeds become incorporated into wine during the vinification process. Red wine is made by maintaining contact between the fermenting liquor and the crushed grape residue (pomace) for prolonged periods, whilst in the manufacture of white wine the grape skins are removed relatively quickly. Accordingly, wine in general, and red wine in particular, contains reasonable amounts of polyphenols, amounting to about 1–3 g/L and is thus a potential commercial source of polyphenolic compounds.

Polyphenols are known to have antioxidant properties and have potential use in the food, cosmetic and pharmaceutical industries. Among the polyphenols, the flavonols have been shown to have many useful properties as antioxidants, and to decrease platelet stickiness.

Epidemiological studies have shown that countries and people with a high flavonol intake have less coronary heart disease (Hertog et al, 1995 Arch. Int. Med. 155, 381–6).

In unprocessed fruit and vegetables the flavonols occur as glycosides and the aglycone is absent. The most abundant flavonol is quercetin. Among vegetables the highest concentration of quercetin glycosides is in onions (3 to 500 mg/kg), kale (100 mg/kg) French beans (30 to 45 mg/kg), and broccoli (30 mg/kg). Among fruit examined quercetin concentration averages 15 mg/kg, with apples having the highest concentration of 21 to 72 mg/kg (Hertog et al, 1992 J. Ag. Food Chem. 40, 2379–83).

Flavonol glycosides are present in grapes and values ranging from 8 to 97 mg/Kg fresh weight have been reported (Macheix et al, 1990 Fruit Phenolics pp 378 CRC Press Boca Raton). During the fermentation process, some of the sugar is split off and the aglycone formed. On average about 50% of the flavonol exists in wine as the aglycone. The flavonol content of grape skins and wine is very variable and depends on the variety of grape and more especially the amount of sunshine in which the grapes are grown. The flavonols have a yellow color and act as filters to blue and ultraviolet light which is very injurious to the grape. During periods of intense sunlight more flavonols are synthesized to protect the grape, and consequently the grape skins and the wine from which it is made has a high concentration of flavonols (Price et al, Am. J. Enol. Vitic. 46 187–194, 1995).

Some wines in France have only 5 mg/L flavonol (calculated as aglycone) whereas up to 150 mg/L have been reported in some Californian wines. The flavonols are virtually absent from the pulp and grape seeds and only trace quantities are present in commercial anthocyanin powders extracted from pomace after making red wine.

Although grape juice is often less rich in polyphenols than wine, it contains flavonols and is a readily available commodity, and can also be used as a source of polyphenols.

Most flavonols enter the diet as glycosides with the glucosides and rutin as the most common flavonols consumed (Bokkenheuser and Winter, 1988 Prog. Clin. Biol. Res., 280 142–148). The absorption of flavonols in man has been a matter of some controversy. It was estimated that the absorption of quercetin aglycone was only 0.3 to 0.5%. Thus with an intake of 50 mg, only some 0.25 mg would be absorbed (Formica et al Fd. Chem. Toxic. 1995 33 1061–1080). However recent work in ileostomy subjects showed that the absorption of quercetin aglycone was 25% and the absorption of quercetin from onions (where it exists chiefly as the glucoside) was 52% (Hollman et al Am. J. Clin. Nutr. 1995 62, 1276–1282). More recently it has been shown that the glucoside is more rapidly absorbed than the rutinoside (Hollman et al, 1997 Crit. Reviews in Science & Nutrition 37, 719–738). One of the reasons for the poor absorption of flavonols either as the aglycone or the glycosides is that they are almost insoluble in water and lipid solvents, although sparingly soluble in ethanol. Thus, on oral administration, a very high proportion of the flavonols are excreted because they are in a physical state which does not favour absorption. Thus, whilst the flavonols are considered pharmacologically beneficial, they are poorly absorbed because they are generally of low solubility. If the flavonols could be made available in a water-soluble form they would be absorbed more easily and be biologically available following oral consumption.

The anthocyanins are water soluble pigments which are responsible for the attractive colors of many flowers, fruit and leaves. They can be easily extracted from plants by acidified alcoholic solvents and many are available commercially as food colorants. They are usually supplied with malto dextrin as a diluent in a concentration suitable for inclusion in beverages or other foods (Timberlake 1980 Food Chemistry 5, 69–80).

The anthocyanins are known to react with the flavonol glycosides in a phenomenon which is described as co-pigmentation (Scheffeldt et al 1978, J. Food Science 43, 517–520). For example, rutin was found to intensify the colour of malvidin—3, 5, diglycoside and to shift the maximum peak of absorption. The process is believed to be the result of a hydrogen bonding mechanism.

Although the flavonols are insoluble in water, they exist in wine in quite high concentrations which vary according to the type of grape used and country of origin (McDonald et al, J. Agric. Food Chem. 1998 46, 368–375). The concentration of total flavonols (expressed as the algycone) in wine was found to range from 4.6 to 41.6 mg/L. Since wine contains about 12% ethanol, and flavonols are soluble in ethanol, it was reasonable to suppose that the relatively high solubility of flavonols in wine was due to the presence of ethanol.

It would be a great advantage to provide flavonols for oral administration in a soluble form, in water or aqueous mixtures or alternatively to increase the concentration of flavonols in ethanol containing beverages. Being in a soluble form would make possible the use of flavonols in beverages, and potentially increase their bio-availability.

SUMMARY OF THE INVENTION

In a first aspect the invention provides a method of increasing the solubility in water of a flavonol component of a flavonol-containing composition, the method comprising the steps of: providing a flavonol-containing composition; providing an anthocyanin-containing composition; and mixing the two compositions. The inventor has found that the presence of anthocyanin in a composition significantly increases the water-solubility (and hence bio-availability) of flavonols, especially at neutral or acidic pH values.

In a second aspect, the invention provides a method of providing an aqueous solution comprising dissolved flavonols at a concentration in excess of 10 mg/L (preferably over 20 mg/L, more preferably over 50 mg/L, and most preferably over 100 mg/L), the method including the steps of mixing, in any order, water, a flavonol and an anthocyanin; and forming an aqueous solution from the mixture comprising the flavonol dissolved in the solution at a concentration in excess of 10 mg/L.

BRIEF DESCRIPTION OF THE DRAWINGS

The invention is further described by way of illustrative example and with reference to the accompanying drawings, in which.

DETAILED DESCRIPTION OF THE INVENTION

In a first aspect the invention provides a method of increasing the solubility in water of a flavonol component of a flavonol-containing composition, the method comprising the steps of: providing a flavonol-containing composition; providing an anthocyanin-containing composition; and mixing the two compositions. The inventor has found that the presence of anthocyanin in a composition significantly increases the water-solubility (and hence bio-availability) of flavonols, especially at neutral or acidic pH values.

Figure 1:
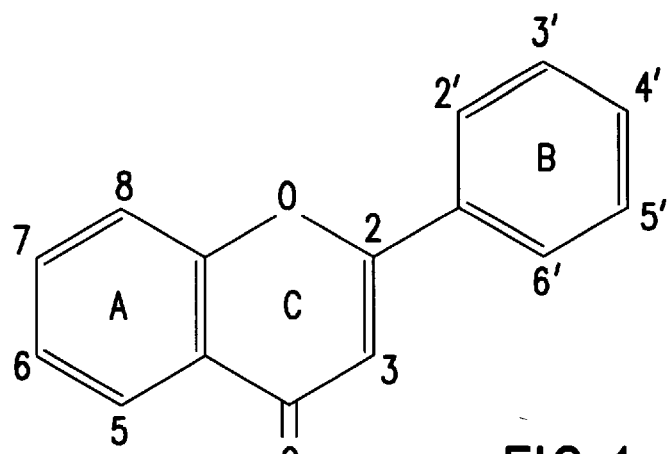
FIG. 1 is a schematic illustration of the core structure of flavones.
Figure 2:
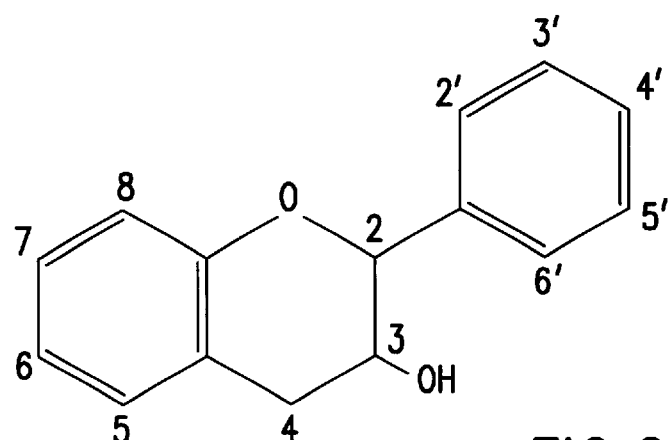
FIG. 2 is a schematic illustration of the core structure of flavanols.
Figure 3:
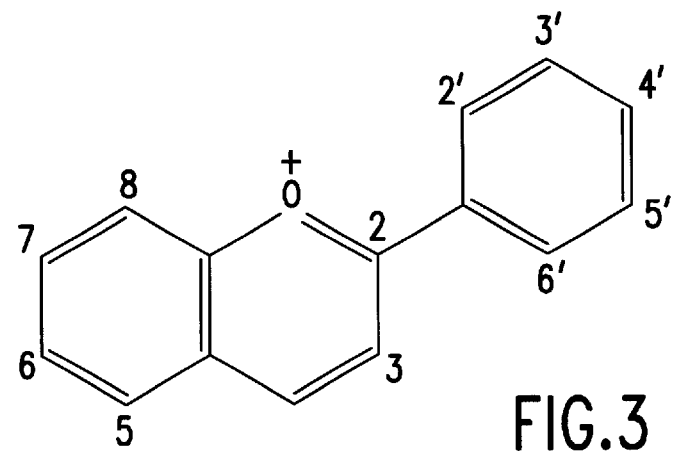
FIG. 3 is a schematic illustration of the core structure of anthocyanins.

The term 'flavonol' as used herein refers to compounds having the structure shown in FIG. 1 and being hydroxylated at one or more of positions 3, 5, 7, 3' 4' or 5'. The term 'flavonol' is also intended to encompass associated derivatives which are additionally substituted, especially those compounds which comprise one or more sugar residues (such as glucose, galactose, arabinose, rhamnose and the like), particularly O-glycosylated compounds. Other compounds, falling within the definition of "flavonol" as used herein, include those comprising other substituent groups such as alkyl (especially methyl), alkoxy (especially methoxy) sulphyl and malonyl groups.

Preferably the flavonol content of the composition comprises the compound kaempferol, myricetin or, most preferably, quercetin or a structural analogue thereof. It will be understood from the foregoing that reference to quercetin is intended to encompass the aglycone, or any glycoside thereof (typically an O-linked glycoside). The glycoside of quercetin tend to have acquired their own trivial names. For example, the rhamnose glycoside of quercetin is known as quercitrin, and the rutinoside is known as rutin. Analogues of quercetin include those compounds which comprise a substituting group other than an —OH group at one or more of the positions 3, 5, 7, 3' and 4'. Other possible substituting groups include: lower alkyl (i.e. less than 5 carbon atoms) especially methyl or ethyl; acetyl; sulphyl; and malonyl. Desirably, in analogues of quercetin only a few (i.e. preferably only one or two) of the positions are substituted with anything other than —OH groups.

Flavonols such as quercetin and glycosides thereof, such as quercetin glucosides, quercitrin (quercetin rhamnoside) and rutin (quercetin rutinoside), are readily available from chemical suppliers (e.g. Sigma, UK and Indofine Inc, USA) ranging from 85–99% purity.

[The glycosides can be expressed as the aglycone by multiplying their concentration by:

$$\left(\text{FW quercetin} \div \text{FW quercitrin} = \frac{302}{448} = 0.674\right)$$

(FW=formula weight). The total flavonol content is the sum of the aglycone contents in the free and conjugated forms.]

Alternatively, as flavonols in general (including quercetin) are present in many naturally occurring substances, such as foodstuffs, the composition of the invention may comprise a flavonol (especially quercetin) obtained from a naturally occurring source. Foodstuffs which contain quercetin in relatively large amounts include certain fruit and vegetables, such as apples, onions and red wine. In particular therefore, the composition of the invention may comprise a flavonol content derived from plants. By way of explanation, such plant-derived compositions may comprise extracts of plants or parts thereof (such as tubers, fruit) which are processed in some way (e.g. by fermentation). Thus, plant-derived compositions include aqueous or organic solvent extracts of plants or parts thereof, fruit juices and fermented liquors (e.g. wine) produced from plants or fruit juice, or compositions obtained from any of the foregoing. The plant material is typically processed (physically and/or chemically) during production of the composition to extract flavonols from the plant and so increase and enrich the flavonol content of the composition. It will be appreciated by those skilled in the art that the invention is not intended to encompass within its scope naturally occurring foodstuffs or plant materials which have not been subjected to processing in any way.

Advantageously the flavonol-containing composition may be such that the plant-derived material comprises at least 25% polyphenols, more preferably 35% polyphenols or most preferably at least 45% polyphenols.

The flavonol-containing composition may be comprised wholly or substantially of the plant-derived material from which the flavonol content of the composition is obtained. Alternatively, the composition may comprise other material, such as flavorings, excipients, carriers and the like conventionally used in formulating compositions for human consumption.

Typically the flavonol content of the composition as a whole is at least 0.1% w/w, preferably at least 1% w/w, more preferably at least 5% w/w, and most preferably at least 10% w/w.

The term "anthocyanin" as used herein is intended to refer not only to monomeric anthocyanins, but also refers to dimeric and polymeric (i.e. containing from 3 to 20 anthocyanidin monomer residues) forms of anthocyanins and to leucoanthocyanidins (also known as flavan-3, 4-diols). The anthocyanins may comprise substitutions (e.g. alkyl, alkoxy groups etc.) and in particular may be O-glycosylated, in a manner similar to that of the flavonols, as described above.

The amount of anthocyanin added to the composition should ideally be carefully controlled. As anthocyanins are generally highly pigmented, their presence in high concentrations in certain foods, drinks or food supplements may be undesirable if it is preferred to avoid the color associated with the presence of anthocyanins. Accordingly it may be preferred in many embodiments to add the minimum amount of anthocyanin consistent with achieving the required level of solubilisation of flavonol. Additionally, or alternatively, it may be desirable to include some other component which masks or hides the color associated with the anthocyanin— such a component could conveniently be another coloring or other substance suitable for human consumption.

The anthocyanin in the composition may be a single anthocyanin, or comprise a mixture of anthocyanins. Preferably the anthocyanin is selected from the group consisting of: malvidin, cyanidin, delphinidin, paeonidin, pelargonidin and petunidin, and glycosides thereof A typical example is malvin (malvidin diglucoside) chloride, which is commercially available in a purified form. Alternatively the anthocyanin may be obtained by extracting anthocyanin containing plants such as grape, black carrot, red cabbage, blackberry, blackcurrent, cranberry and the like.

Those skilled in the art will know of the many methods which are employed for extracting anthocyanins since they are widely used for preparing food colorants. The anthocyanin in the composition can be in highly purified form, or a mixture with other polyphenols especially flavonols, or with a diluent such as maltodextrin. It is preferred that the content of anthocyanin in the composition as a whole is at least 1% (w/w), more preferably at least 5%, and most preferably at least 10%. The content of anthocyanin in the composition should typically be sufficient to solubilize in water at least 0.1% w/w flavonol, preferably sufficient to solubilise at least 1% w/w flavonol in said composition.

Preferably, Where the method involves mixing of a flavonol-containing composition with an aqueous solution of anthocyanins, the aqueous solution will conveniently comprise anthocyanin dissolved at a concentration of at least 10 mg/L, more preferably at least 50 mg/L, and most preferably at least 100 mg/L.

It will be apparent to those skilled in the art that the order of addition of the flavonol and anthocyanins is not critical. Thus, for example, one may prepare an anthocyanin-containing composition and add to that composition a suitable amount of flavonol, or vice versa. In general however, in view of the poor solubility of flavonols, it will normally be preferred to add the flavonol-containing composition to the anthocyanin-containing composition such that the anthocyanins will be present in excess, at least initially, which will tend to prevent clumping of solid flavonol in the mixture and so facilitate mixing.

It may be preferred that a slight excess of anthocyanin will be present after mixing of the two compositions has been completed, so as to ensure solubilisation of at least the desired amount of flavonol.

In one particular embodiment, the method comprises the fortification of compositions (such as red wine or dealcoholised red wine) with additional flavonol, simply by the addition of extra flavonol to a pre-existing flavonol/anthocyanin composition (e.g. red wine), provided that there is sufficient anthocyanin in the pre-existing composition to solubilise the extra added flavonol. If there is insufficient excess anthocyanin already in the pre-existing composition, one may simply add a suitable additional amount of additional anthocyanin.

However wines are comparatively expensive materials, and anthocyanins are present in high concentrations in fruit and vegetable juices, such as grape, cranberry, blackcurrant and blackberry juices. In preferred embodiments the invention will comprise the addition of flavonols (such as quercetin) to fruit and/or vegetable juices, so as to fortify the fruit or vegetable juice with additional flavonol.

In some embodiments it may be desirable to facilitate initial dissolution of the flavonols. This can be achieved, for example, by adding ethanol to the composition or by initially dissolving the flavonols in a small amount of ethanol and adding the ethanol-dissolved flavonols to the rest of the composition. Additionally or alternatively, the composition may be heated (e.g. to 50° C. for about 30 minutes, or to 75° C. for about 10 minutes, or to 100° C. for about 1 minute). The application of heat may be especially preferred if it is desired to provide an ethanol-free flavonol containing composition.

The composition prepared by the method of the invention, when dry, is typically solid at atmospheric pressure (760 mm Hg) throughout the temperature range 10–20° C. The composition may be particulate (e.g. powdered or granulated), or may be formed into capsules, tablets and the like.

Alternatively the composition may be a liquid comprising water or other aqueous solvent such as aqueous ethanol. The inventor has surprisingly found that compositions prepared in accordance with the method of the invention present flavonols in a more soluble form in aqueous solutions. Flavonols are almost insoluble in water at pH 7.0 or below, but in the presence of anthocyanin, their solubility is markedly increased, and the flavonols are rendered bio-available.

Moreover, when a composition containing both a flavonol (e.g. quercetin) and anthocyanin is administered to volunteers for 4 weeks, the plasma antioxidant capacity of the volunteers is significantly increased (as determined by the FRAP assay, described below).

The flavonol-containing composition may comprise flavonols (including quercetin) obtained from grapes (whole grapes or parts thereof, such as skins or juice), wine (especially red wine, which comprises much higher concentrations of polyphenols than white wine), or by-products and/or waste products of the wine-making process, such as pomace (i.e. the residue of crushed grapes following juice extraction) or marc (waste solids remaining after initial fermentation). However, flavonols such as quercetin are present in a wide range of naturally occurring materials, many of which contain a higher flavonol content than red wine and are considerably cheaper, and so present more appropriate sources of flavonol. Examples of such materials include: fruit in general, such as apples (e.g. var. "Gravensteiner"); especially apple peel; pears (e.g. var. "Williams Christs"); bell peppers (e.g. var. "Yolo wonder"; redcurrants; blackcurrants (particularly preferred as being relatively high in flavonols); lemons; cherries; cranberries; gooseberries; tomatoes; olives; and vegetables in general, including: radishes (e.g. var. "Saxa treib"); kohlrabi (e.vg. var. "Primavera"); horseradish; potatoes; onions; and asparagus.

In a one embodiment of the invention, the flavonol-containing composition is derived from a red wine and comprises a representative profile of substantially all the flavonol compounds present in the wine (typically, although not necessarily, present in the composition substantially in the relative amounts representative of those in the wine from which the composition is derived). Such a composition may be referred to as a "total flavonol pool" of the wine.

Flavonols may conveniently be obtained from red wine or other flavonol-containing liquids (such as fruit or vegetable extracts) by absorption onto a chromatographic resin column, with elution of the polyphenol-enriched fraction from the column (typically following a washing step) by use of a 40–50% ethanol eluent, or other suitable organic solvent (such as methanol, acetone, ethyl acetate, dimethylene chloride, and chloroform—which may be in aqueous solution). The organic solvent is preferably relatively volatile (i.e. having a boiling point of between 30 and 85° C. at 760 mm Hg pressure) and so readily driven off, to leave a substantially dry (i.e. less than 10% w/w $H_2O$) solid composition comprising flavonols. Such a method may successfully be used to obtain a total flavonol pool from red wine.

Alternatively, flavonols may be obtained from red wine or other flavonol-containing liquid by solvent extraction using a suitable organic solvent immiscible with the wine or other liquid. Alternatively, flavonols may be obtained from flavonol-containing solids by solvent extraction (typically extraction with an organic solvent such as ethanol or ethyl acetate)—the solid can then be separated from the solvent by filtration or centrifugation. The solvent may then be evaporated to leave a substantially dry, solid composition comprising flavonols.

Alternatively the flavonols may be obtained in purified form (e.g. 85–99% pure) from a chemical manufacturer, providing that the material is suitable for human consumption.

In preferred embodiments, the composition obtained by mixing the flavonol-containing and the anthocyanin-containing compositions is presented as a food supplement. This may be a substance to add as an additional ingredient during manufacture of the foodstuff, or may be a separate substance to be consumed by an individual (e.g. as a tablet or capsule) substantially in isolation from (i.e. not mixed with) other food components prior to consumption (although, of course, the tablet or capsule may be taken with food). The invention thus includes within its scope a prepared product, particularly a prepared foodstuff (i.e. one which is not naturally occurring) comprising a composition in accordance with the invention, which may be in the form of a solid or a drink (e.g. a flavonol-fortified fruit or vegetable juice). Alternatively, the composition may be presented as a solid to be made into a drink by mixing with a physiologically acceptable diluent (such as milk, water, solutions or gels prepared from Aloe vera, or other aqueous liquid).

The dosage of composition given to a subject is dependent on the degree of activity of the material but will normally be between 10 mg and 10 g per day. The preferred dose of flavonol will be in the range 0.1–1000 mg per day, preferably in the range 0.5–500 mg per day, more preferably in the range 2–250 mg per day.

Compositions obtained by mixing the flavonol-containing and anthocyanin-containing compositions in accordance with the invention, may be prepared in accordance with conventional food supplement or pharmaceutical practice. The diluents, excipients or carriers etc. which may be used are well known in the formulation art and the form chosen for any particular regimen will depend on the given context and the formulator's preferences. In general the dose will depend on the concentration of flavonols (particularly quercetin) in the composition, and the identity of the flavonol compounds in question.

Moreover, the compositions may comprise any number of further components, such as those typically used in the food industry and/or in the pharmaceutical industry. Such components may include nutrients (especially trace elements and vitamins), antioxidants, therapeutic substances (especially those having a therapeutic effect in relation to prevention and/or treatment of CHD, in particular, aspirin), flavoring, and sweeteners (especially artificial sweeteners, such as aspartame etc.).

Examples of the above include the following: a carotenoid such as lutein, lycopene, or α-and/or β-carotene; antioxidant nutrients or anti-inflammatory agents such as vitamin A, vitamin C, vitamin E(α-tocopherol and other active tocopherols), folic acid, selenium, copper, zinc, manganese, ubiquinone (coenzyme Q10), salicylic acid, 2,3-dihydroxy benzoic acid, and 2,5-dihydroxy benzoic acid.

Antioxidants such as carotenoids and vitamin E are partially destroyed in the gastro-intestinal tract by oxidation. By inclusion of these compounds in the composition of the invention it is believed that this process is inhibited and more antioxidants are absorbed. Use of a composition comprising α-tocopherol and/or aspirin is especially preferred since it is believed that such a mixture afforts a synergistic-effect in the presence of flavonols.

Typical suitable daily dose of these additional components of the composition (and which may therefore be included in the composition such that normal consumption of the composition will give the appropriate dose) are as follows:

| | |
|---|---|
| Lutein | 2 to 50 mg e.g. conveniently 7.5 mg |
| Beta carotene | 2 to 20 mg e.g. conveniently 5 mg |
| Vitamin A | 400 to 600 RE e.g. conveniently 500 RE |
| Vitamin C | 75 to 250 mg e.g. conveniently 100 mg |
| Folic Acid | 0.1 to 1.0 mg e.g. conveniently 0.2 mg |
| Selenium | 80 to 120 µg e.g. conveniently 90 µg |
| Copper | 2 to 4 mg e.g. conveniently 3 mg |
| Zinc | 10 to 20 mg e.g. conveniently 15 mg |
| Coenzyme Q10 | 10 to 200 mg e.g. conveniently 30 mg |
| Aspirin | 10 to 150 mg e.g. conveniently 75 mg |

Thus, in one embodiment the composition takes the form of capsules, each capsule containing 50 mg of flavonol composition, with a suggested intake of one to four capsules per day. Another presentation is as a non-alcoholic drink which provides an effective dose of flavonols when dissolved in water (still or aerated) flavored and sweetened to taste, or dissolved in a fruit juice e.g. grape, apple or orange etc., or in solutions or gels prepared from Aloe vera.

Whilst it may be preferred for a number of reasons (e.g. social, religious and economic) to provide an alcohol-free drink comprising the composition of the invention, such drinks can be fortified with alcohol (e.g. from vodka, gin, whisky) to give a desirable level of 5–50% alcohol depending on the consumer's taste.

Other presentations are as a food ingredient in dairy products such as milk and yogurts, preserves, and dietary products intended as meal supplements or replacements. The above examples are illustrative only and are not intended to be limiting in any way.

In a second aspect, the invention provides a method of providing an aqueous solution comprising dissolved flavonols at a concentration in excess of 10 mg/L (preferably over 20 mg/L, more preferably over 50 mg/L, and most preferably over 100 mg/L), the method including the steps of mixing, in any order, water, a flavonol and an anthocyanin; and forming an aqueous solution from the mixture comprising the flavonol dissolved in the solution at a concentration in excess of 10 mg/L.

Conveniently the aqueous solution does not contain any organic solvent and in particular is preferably substantially free of ethanol, such that the solubilisation of the flavonol in water is primarily due to the presence of the anthocyanin.

The aqueous solution prepared by the method of the second aspect of the invention is safe for human consumption, and will typically be formulated as a drink, comprising optional ingredients such as anti-oxidants, flavoring agents, sweeteners, vitamins or minerals as described previously.

As explained previously, heat may advantageously be used to facilitate the initial dissolution of the flavonols, which substantially remain in solution upon cooling to room temperature. Alternatively, and less preferably, ethanol may be used to assist dissolving the flavonols. The method may be particularly advantageous when producing an aqueous solution of dissolved flavonols at neutral or acidic pH.

EXAMPLES

Example 1

The Solubilization of Quercetin in Wine and Fruit Juices by the Addition of an Ethanolic Solution of Quercetin The purpose of the investigation was to determine the solubility of quercetin in red wine, a white wine and two fruit juices when the added quercetin was dissolved in ethanol. The quercitin used in this example and in others was quercetin dihydrate ($C_{15}H_{14}O_9$, FW 238, Sigma, UK).

The solubility of quercetin is expressed as the anhydrous molecule ($C_{15}H_{10}O_7$, FW 302). An ethanolic solution of quercetin was prepared and added in slight excess to red wine, white wine, cranberry juice and blackcurrant juice, at room temperature. After centrifugation to remove solid quercitin, the optical density was measured in a spectrophotometer at 258 nm and 375 nm. At these wavelengths quercetin has maximum absorption and its concentration can be calculated using the factor $\log_{epsilon}=2.75$.

The procedure was as follows: a stock solution of quercetin dihydrate in absolute ethanol was prepared containing 5 mg quercetin dihydrate per ml. Aliquots of 50 µL of this solution were added to 5ml of the liquids being examined. The mixtures were then vigorously stirred on a Vortex mixer and allowed to stand for 20 to 30 min at room temperature for a precipitate to form.

The mixture was then centrifuged at 2000×g for 30 min at 20° C. Aliquots were then taken and the optical density measured in a spectrophotometer (Camlab, UK) at 258 nm and 375 nm, diluting where necessary with an appropriate diluent e.g. water for fruit juices, 12% ethanol for wines etc. In addition, 50 µL ethanol was added to 5 ml of each of the liquids being examined and the optical densities determined likewise. The controls were water and 12% ethanol. The solubilities of quercetin in the liquids were determined from the differences between the optical densities of the liquids with and without quercetin.

The solubility of quercetin in the wines and fruit juices examined are shown in Table 1.

Quercetin is almost insoluble in water (1 mg/L) and very sparingly soluble in 12% ethanol (5 mg/L). However quercetin is much more soluble in red wine (40 mg/L), cranberry (35 mg/L) and blackcurrant juices (28 mg/L). Quercetin was not more soluble in white wine (5 mg/L) than in 12% ethanol.

TABLE 1

Solubility of quercetin in fruit juices, after the addition of an ethanolic solution of quercetin

| Liquid | Solubility of Quercetin[a] mg/L | |
|---|---|---|
| | 258 nm[b] | 375 nm[b] |
| Red wine[c] (Cabernet Sauvignon) | 44.1 | 39.8 |
| White wine[c] (Vin Ordinaire) | 4.2 | 5.4 |
| Cranberry juice[d] | 33.6 | 34.7 |
| Blackcurrant juice[e] | 28.1 | 31.0 |
| Ethanol 12% v/v | 4.1 | 5.3 |
| Water | 2.2 | 1.8 |

[a]Values expressed as the anhydrous compound
[b]Wavelengths of optical density measurement
[c]French wines
[d]Ocean Spray ™ brand
[e]Ribena ™ brand Since white wine does not contain significant amounts of polyphenols, it would appear that the quercitin is solubilized by polyphenols present in red wine and fruit juices, possibly by formation of a soluble complex.

The method of adding quercitin to a red wine or fruit juices containing polyphenols is a practical means of fortifying drinks with a flavonol, such that the flavonol is available in solution. Because flavonols are almost insoluble in water or dilute aqueous ethanol it is impracticable to provide flavonols in these solvents since if solid flavonol is added most of it does not dissolve but sinks to the bottom of the vessel.

Example 2

The Solubilization of Quercetin in an Aqueous Solution of Grape Anthocyanin, following the Addition of Excess Quercetin in an Ethanolic Solution The purpose of this investigation was to examine the solubility of quercitin in grape anthocyanin which is a major component of the polyphenols in red wine and coloured fruit juices.

The grape anthocyanin powder was a commercial product used as a food colorant (Phytone Ltd, Burton on Trent, UK) and had an anthocyanin content of 3.94%.

The procedure used was as follows: anthocyanin powder was dissolved in deionised water to give concentrations of 0.625, 1.25, 2.5, 10 and 20 mg/ml. A stock solution of quercetin dihydrate (5 mg/ml) in absolute ethanol was also prepared. To each 5 ml of the above anthocyanin solution was added 133 µL of the quercetin solution at room temperature, followed by increasing aliquots of 30 µL until a precipitate was clearly visible. The mixtures were allowed to stand for 20 to 30 min and then centrifuged at 2000×g for 30 min at 20° C. The optical densities were measured at 258 nm and 375 nm as in Example 1. To 5 ml of each corresponding anthocyanin solution was added the same volume of ethanol determined above to give a precipitate, and the optical densities measured. The concentration of quercetin was determined from the difference in optical density between the solutions with or without quercetin. The control was water.

Figure 4:
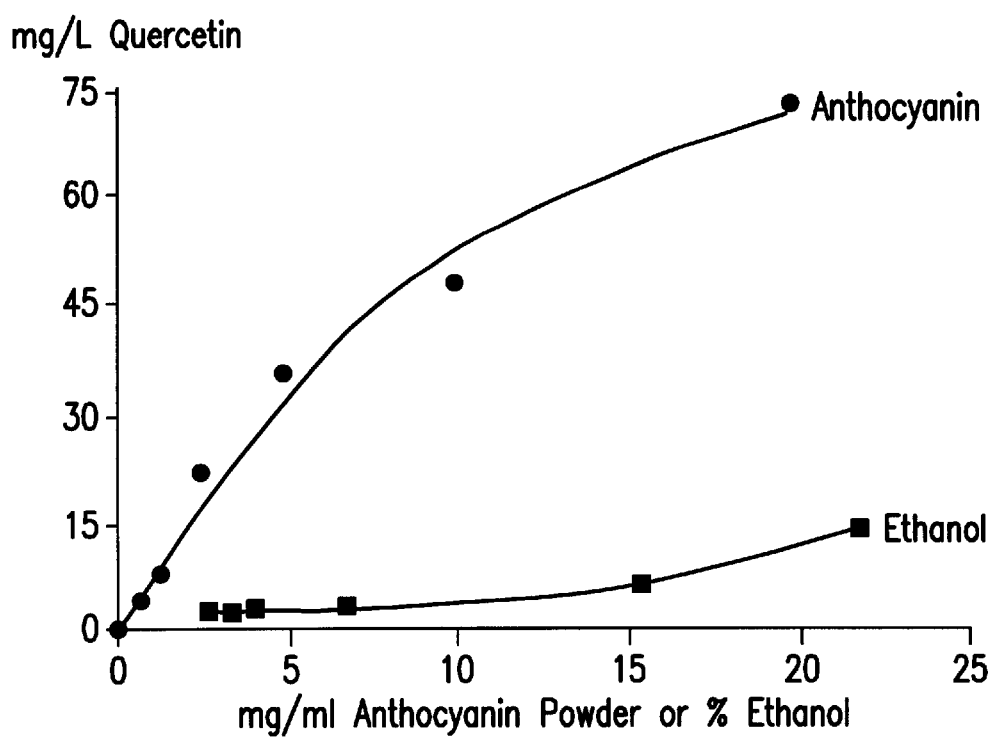
FIG. 4 shows a graph of the solubility of quercetin in an aqueous solution of grape-derived anthocyanin powder (containing 3.94% anthocyanin), following the addition of excess quercetin in an ethanolic solution.

Since quercitin is more soluble in aqueous ethanol than water a further series of controls were prepared in which quercetin in ethanol was added to water in amounts corresponding to those used in the test, and the solubilities likewise determined. As shown in FIG. 4 the solubility of quercetin increased in almost linear fashion with increasing concentration of anthocyanin powder (at least at low [<10 mg/ml] anthocyanin powder concentration). With 20 mg anthocyanin powder/ml the solubility of quercetin was 75 mg/L. This was in a 22% ethanol solution. Without anthocyanin present the solubility of quercetin is only 13 mg/L. The commercial anthocyanin powder contained 3.94% anthocyanin. Thus in the 20 mg/ml solution the concentration of anthocyanin was 800 mg/L. Thus the ratio of quercetin: anthocyanin in the solution was 1:10.7. To solubilize quercetin more anthocyanin was needed than quercetin w/w.

It is concluded that flavonols are readily soluble in aqueous solution of anthocyanin when the quercetin is added as an ethanolic solution. Since anthocyanin powders are readily available commercially, it is practical to supplement drinks containing anthocyanin with quercetin in a soluble form.

Example 3

The solubilization of Quercetin in Different Anthocyanin Containing Liquids by Means of Heat Although it is convenient to add quercetin in ethanolic solution to anthocyanins, the method increased the ethanol content of the beverage. An investigation was made into the possibility of dissolving quercetin, without the use of ethanol.

The procedure was follows: aliquots (20 ml) of the liquids examined were placed in a plastic tube with 50 mg solid quercetin dihydrate and rotated at room temperature (20° C.) for 3 hours followed by centrifugation at 2000×g for 30 min at 20° C. Quercetin concentration was measured as in previous examples from the difference in optical density at 375 nm of liquids with and without quercitin.

The solubility of quercetin when mixed with anthocyanin containing solutions at room temperature was extremely small (Table 2). For red wine the solubility of quercetin was only 3 mg/L and for grape anthocyanin powder (1 g/L) only 0.7 mg/L.

To investigate dissolution by heat, the liquids were heated in a sealed tube for 1 min in a microwave oven (when boiling of the liquid occurred) and cooled to room temperature. Under these conditions (see Table 2), quercetin was much more soluble, and the solubility of quercetin was comparable to that achieved by the previous methods using ethanolic solution of quercitin (Table 1).

Anthocyanin concentrations of the liquids were also determined by the method of Miketic-Aleksic et al 1972, Lebensm-Wiss.u Technol. 5 163–165). The method consists of diluting 1 ml aliquots of wine or juice with a buffer at pH1 and measuring the optical density at 520 nm. Results were calculated as malvidin-3-glucoside (FW. 493.5) using the extinction coefficient of 28,000. For solids, a known weight of powder was dissolved in buffer at pH1 and the results obtained as g anthocyanin/100 g powder.

Samples of red wine, grape anthocyanin and grape seed extract were analyzed for polyphenols by means of HPLC by ETS Laboratories, St Helena, Calif. 94574, USA. The four red wines and rose wine all produced a higher solubility of quercetin than in 12% ethanol. The three wines above 150 g anthocyanin/L gave a greater solubility than the two wines below 150 g anthocyanin/L. There was no increase in the solubility of quercetin in white wine (in which anthocyanin is substantially absent). The highest solubility was in blackcurrant juice, which also had the highest anthocyanin content. The four fruit juices all contained anthocyanin and gave an increase in solubility of quercetin. Quercitin also demonstrated increased solubility in a grape anthocyanin solution, which was comparable to that of the wines and fruit juices. White wines in which anthocyanin was absent were similar in effect to 12% ethanol.

Whilst anthocyanin powder had a positive effect on solubility, grape seed extract which does not contain anthocyanin was ineffective.

The method of providing a beverage enriched in flavonol is simple and requires only a brief period of heating. Moreover it leaves the liquids relatively unchanged in composition, and does not increase the ethanol content.

Table 3 shows results of the polyphenol analysis by HPLC. All three samples, red wine, grape anthocyanin and grape seed extract, contained appreciable amounts of polymeric phenols. Red wine and grape seed extract contained flavanols (catechin, epicatechin) and procyanidin dimers. Red wine and grape anthocyanin contained anthocyanin monomers and polymers. Since grape seed extract was inactive in increasing the solubility of quercetin, it was concluded that it is the anthocyanins which are the solubilizing factor, and these are present in red wine and the grape anthocyanin powder, but are absent from the grape seed extract.

TABLE 2

Solubility of quercetin in different liquids

| Liquids | Solubility of quercetin mg/L | | Anthocyanin present mg/L |
|---|---|---|---|
| | Room temp | Boiling | |
| Controls | | | |
| Water | 0.3 | 2 | 0 |
| Ethanol 12% v/v | 1 | 3 | 0 |
| Red wine[b] | | | |
| Cabernet-Sauvignon (F) | 3 | 36 | 196 |
| Cabernet-Sauvignon (ARG) | | 18 | 224 |
| Rhone (F) | | 19 | 271 |
| Shiraz (AUS) | | 11 | 118 |
| Rosé[b] | | | |
| Rosé D'Anjou (F) | | 9 | 138 |
| White[b] | | | |
| Vin Ordinaire (F) | 0 | 4 | 0 |
| Chardonnay (AUS) | | 6 | 0 |
| Fruit juices | | | |
| Cranberry[c] | 0 | 12 | 109 |
| Cranberry-blackcurrant[c] | | 16 | 155 |
| Grape juice[d] | | 38 | 152 |
| Blackcurrant[e] | | 82 | 307 |
| Polyphenol extracts in water | | | |
| Anthocyanin[f] 1 g/L | 0.7 | 50 | 394 |
| Grape seed[g] | | | |
| 125 g/L | | 4 | 0 |
| 250 g/L | | 4 | 0 |
| 500 g/L | | 6 | 0 |

[a]measured from O.D. at 375 nm
[b]origin of wines: F = France, ARG = Argentine AUS = Australia
[c]Ocean spray ™ brand
[d]Welch's ™ Concord brand
[e]Ribena ™
[f]Vinox ™ (Polyphenolics Inc) solid dissolved in water
[g]Phytone Ltd solid dissolved in water

TABLE 3

Polyphenols in red wine, anthocyanin powder and grape seed extract

| Polyphenols | Red wine mg/L | Grape anthocyanin powder mg/g | Grape seed extract mg/g |
|---|---|---|---|
| 1 gallic acid | 35 | 0.9 | 3.9 |
| 2 procyanidin dimers | 49 | <0.1 | 77.0 |
| 3 catechin | 20 | <0.1 | 74.6 |
| 4 epicatechin | 15 | <0.1 | 51.0 |
| 5 syringic acid | 8 | <0.1 | <0.1 |
| 6 polymeric phenols | 445 | 50.0 | 356 |
| 7 caftaric acid | 12 | 0.2 | <0.1 |
| 8 caffeic acid | 5 | <0.1 | <0.1 |
| 9 coutaric acid | 14 | <0.1 | <0.1 |
| 10 p-coumaric acid | 5 | <0.1 | <0.1 |
| 11 trans resveratrol | 9 | <0.1 | <0.1 |
| 12 cis resveratrol | 2 | <0.1 | <0.1 |
| 13 myricetin glycosides | 2 | <0.1 | <0.1 |
| 14 quercetin glycosides | 8 | 0.5 | 1.8 |
| 15 myricetin | 1 | <0.1 | <0.1 |
| 16 quercitin | 1 | <0.1 | 0.2 |
| 17 delphinidin glycoside | 2 | 4.4 | <0.1 |
| 18 cyanidin glycoside | <1 | 1.7 | <0.1 |
| 19 peonidin glycoside | 2 | 5.2 | <0.1 |
| 20 petunidin glycoside | 2 | 2.8 | <0.1 |
| 21 malvidin glycoside | 7 | 14.0 | <0.1 |
| 22 polymeric anthocyanins | 22 | 4.4 | <0.1 |

Example 4

The Solubilization of Quercetin by Heating Excess Quercetin Solid With Aqueous Solutions of Three Different Commercial Preparations of Anthocyanins Obtained from Grape, Blackcurrant and Red Cabbage.

The purpose of the investigation was to compare the ability of anthocyanin from different sources to solubilize quercitin.

The procedure was as follows: The grape anthocyanin was obtained from Phytone Ltd, UK (as used in example 2). Blackcurrant and red cabbage anthocyanin were obtained from Overseal Ltd, Swadlincote Derbyshire UK. The anthocyanin contents of each powder were measured according to the method of Niketic-Aleksic et al (as in example 3).

Figure 5:
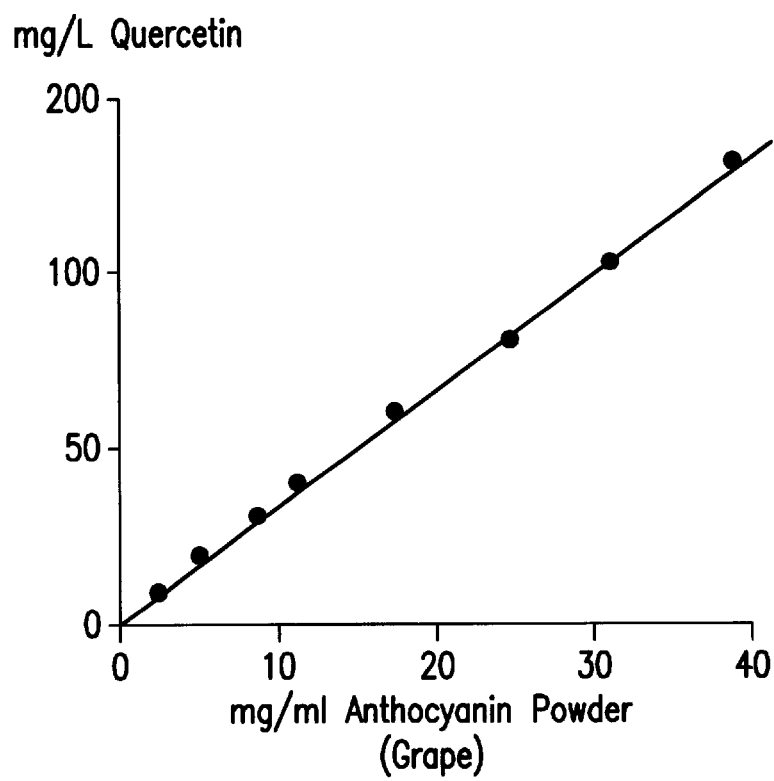
FIG. 5 shows a graph of the solubility of quercetin in an aqueous solution of grape-derived anthocyanin powder (containing 3.94% anthocyanin) in which excess solid quercetin is heated with said solution.
Figure 6:
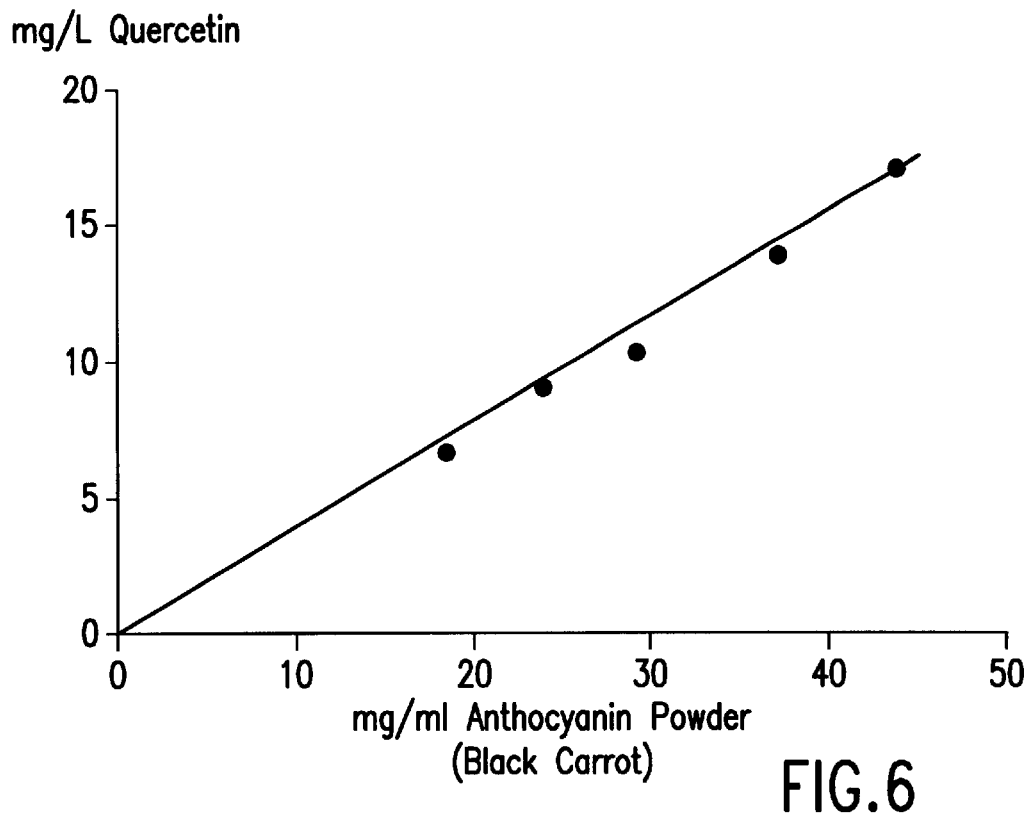
FIG. 6 shows a graph of the solubility of quercetin in an aqueous solution of black carrot-derived anthocyanin powder (containing 1.21% anthocyanin) in which excess solid quercetin is heated with said solution.
Figure 7:
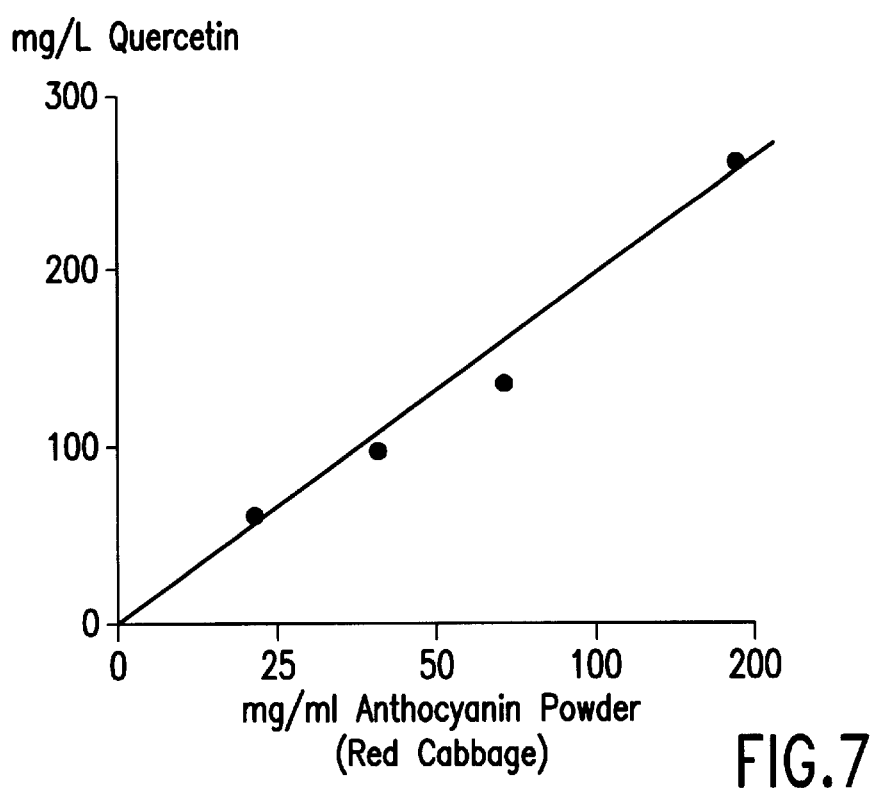
FIG. 7 shows a graph of the solubility of quercetin in an aqueous solution of red cabbage-derived anthocyanin powder (containing 2.51% anthocyanin) in which excess solid quercetin is heated with said solution.

Solutions of the anthocyanins were made in water ranging from 2.5 to 30 mg/ml for grape, 15–40 mg/ml for black carrot and 25 to 150 mg/ml for red cabbage. To 20 ml of each solution was added 50 mg quercetin dihydrate solid and the mixture heated for 1 min in a microwave oven as before, cooled to room temperature and centrifuged at 2000×g for 30 min. Aliquots with and without quercetin were diluted with water 1:9 and the optical density read at 375 nm. The concentration of quercetin was measured by difference in optical density between solutions with and without quercetin as previously. As shown in FIGS. 5 to 7 quercetin was more soluble in all three solutions of anthocyanins than in water alone and the effect was substantially linear with increasing concentrations of anthocyanin powder. The anthocyanin content of the three powders were grape: 3.94 g/100 g, black carrot 1.21 g/100 g, red cabbage 2.51 g/100 g.

The results demonstrate that the increased solubility of quercetin in anthocyanins is a general phenomenon and not restricted only to grape anthocyanins but can be obtained with other suitable edible material that contains anthocyanins.

Example 5

The Solubilization of Quercetin in an Aqueous Solution of Malvin Chloride by the Addition of an Ethanol Solution of Quercitin.

The anthocyanins can be divided into two major classes: the monomeric anthocyanins and the polymeric anthocyanins. A typical example of a monomeric anthocyanin is malvin chloride, a salt of the oxonium ion malvidin-3-glucose and the chloride ion. It can be obtained in a high state of purity (Indofine Inc, USA) and therefore used to determine the solubilizing effect of an anthocyanin monomer. The procedure was as follows: malvin chloride (2.2 mg) was dissolved in 2 ml citrate buffer (pH 3.0)—one ml acted as a control. To the other ml was added stepwise 0.25 $\mu$l ethanol containing 5 mg/ml quercetin dihydrate. Equal amounts of ethanol were added to the control. Each solution was diluted (1:9) with 5% aqueous ethanol and the optical density determined at 275 nm. The quercetin concentration was calculated as in previous examples.

Figure 8:
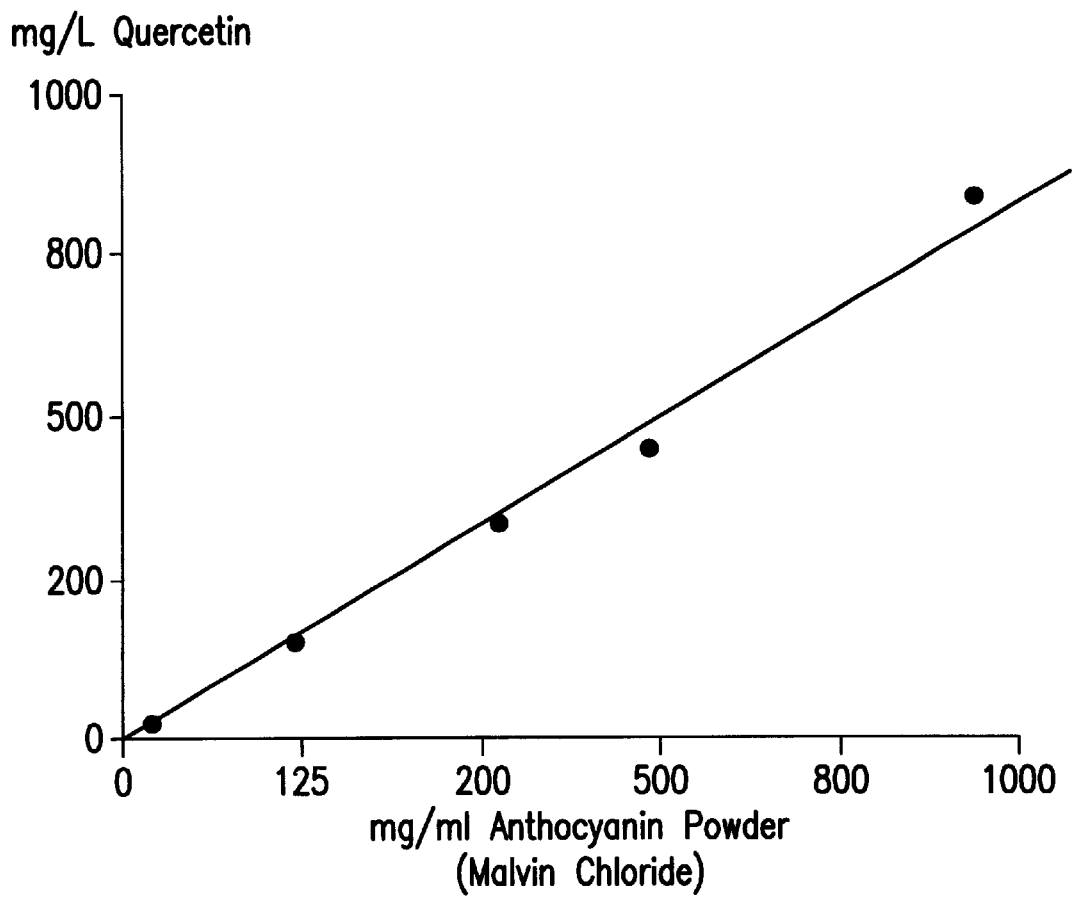
FIG. 8 shows a graph of the solubility of quercetin in an aqueous solution of malvin chloride, following the addition of quercetin in an ethanolic solution.

As shown in FIG. 8, up to 1000 $\mu$g quercetin was added to 1 ml malvin chloride. With 750 $\mu$g quercetin no precipitate of quercetin appeared, but there was a slight precipitate at 1000 $\mu$g which was centrifuged off. The concentration of quercetin in malvin chloride was linear up to 750 $\mu$g.

At this concentration of added ethanol (20% v/v) quercetin is soluble to the extent of 13 mg/L. Thus under these conditions, quercetin is made extremely soluble by the presence of malvin chloride, although it is quite possible that the solution was super saturated since on standing at 4° C. a large precipitate occurred.

Example 6

A Comparison of the Solubilization of Quercetin, Quercitrin and Rutin by Heat in Solutions of Grape Anthocyanin and Malvin Chloride.

Quercetin is a flavonol aglycone. In fruit juices it exists as the glycoside. The purpose of the investigation was to examine the solubilization of glycosides of flavonols by anthocyanins. The three flavonols studied were quercetin dihydrate, quercitrin (quercetin 3-L-rhamnoside, $C_{21}$, $H_{20}$, $O_{11}$, FW 448.4 Sigma UK) and rutin (quercetin 3$\beta$-D-rutinoside hydrate, $C_{27}$, $H_{30}$, $O_{16}$, FW 610.5, Sigma, UK) The procedure was as follows: To 1 ml grape anthocyanin (20 mg/ml) in water was added 2.5 mg of the flavonol and the mixture heated for 1 min in a microwave oven, cooled, centrifuged and the optical density of the supernatant measured at 375 nm. Samples were diluted in water 1:9 before reading. Aliquots of anthocyanin and water with and without the flavonol were treated similarly.

Flavonol concentrations expressed as mg/L quercetin aglycone were calculated from the differences between the solution with and without the added flavonol, as previously.

The same procedure was used for measuring the solubility of the flavonols in malvin chloride. In this case 1.8 mg malvin chloride was dissolved in 2.0 ml citrate buffer at pH3. To 1 ml was added 2 mg of the flavonol, the other 1 ml acted as a control. After heating, the mixture was cooled to room temperature, centrifuged, and the supernatant diluted 1:9 with 50% aqueous ethanol. The optical densities were measured at 375 nm.

As shown in table 4, the solubility of quercitrin and rutin in water was very much higher than quercetin. The solubility of all the flavonols were increased in the presence of grape anthocyanin and malvin chloride. This demonstrated that glycosides of quercetin were more soluble in anthocyanin solutions than in water. Moreover the increased solubility was also seen with a pure anthocyanin monomer, malvin chloride.

TABLE 4

A comparison of the solubilities of quercetin, quercitrin and rutin by heat in solutions of aqueous grape anthocyanin or malvin chloride.

| Flavonol | Water | Grape Anthocyanin Solubility of quercetin aglycone | Malvin chloride in mg/L |
|---|---|---|---|
| Quercetin | 2 | 90 | 28 |
| Quercitrin | 53 | 316 | 127 |
| Rutin | 36 | 260 | 74 |

Example 7

Preparation of Composition from a Red Wine Containing a Low Concentration of Flavonols and Enrichment with Pure Flavonol

The red wine processed was of the Cabernet Sauvignon variety from France. It contained 1.8 g/L polyphenols. The flavonol content (calculated as the aglycone) was 8.8 mg/L (myricetin glycosides 1.1 mg/L, quercetin glycosides 5.4 mg/L, myricetin 1 mg/L, quercetin 1 mg/L).

The powder containing the polyphenols was made as follows: 1 litre of red wine was filtered, rotary evaporated under reduced pressure at 75° C. for one minute, cooled, then rotary evaporated under reduced pressure at 55° C. until the volume was reduced to approximately 150 ml. 50 g of Diaion™ resin (Supelco, UK) was weighed into a beaker covered with methanol and allowed to stand for 15 minutes. The methanol was then decanted off, and replaced with water. After standing for 10 minutes the resin was stacked into a glass column (half filling the column), and washed with water.

The wine concentrate was applied to the column, followed by a water wash (300 ml). The polyphenols were eluted with 50% ethanol. Collection was begun as the colored fraction began to exit the column, and was ended when the eluate was free from color (after a total of 500 ml 50% ethanol had been used). Phenolic content of the eluate at this point was at a concentration of 0.1 mg/L as determined by the Folin-Ciocalteu method (Singleton & Rossi 1965 Amer. J. Enol. & Viticulture 16 144–158).

The phenolic fraction was reduced by rotary evaporation at 50° C. to approximately 120 ml and this was freeze-dried to give the final sample. The yield of powder was 2.24 g/L with a polyphenol content of 45%. The flavonol content was only 4.5 mg aglycone/g polyphenols (0.45% w/w).

Fortification of polyphenol powder with pure flavonol was made as follows: 400 g of the polyphenol powder was dissolved in 10 L deionized water. Quercetin dihydrate (Sigma, UK) amounting to 12 g was dissolved in 3.5 L ethanol and added to the above to give a clear solution. The alcohol was removed by a rotary evaporator under vacuum, and the residue freeze-dried to give a solid with 3–4% moisture content, which was freely soluble in water.

Example 8

The Effect of Adding Quercetin to a Preparation of Red Wine Polyphenols and Administering said Mixture to Volunteers

The purpose of this investigation was to compare the effects of red wine polyphenols with and without added quercetin on the antioxidant capacity of plasma (FRAP) in volunteers.

13 healthy men aged 35 to 65 who were non-smokers, consuming a standard UK diet participated in a private and confidential study. Two weeks before the study the volunteers discontinued wine consumption. All volunteers were asked to maintain their usual diet and lifestyle during the study. The volunteers were divided into three groups A, B and C and given for 4 weeks one of the following—A: (a placebo drink consisting of 36.6 g glucose, 1.1 g citric acid, 0.38 g blackcurrant flavor, 0.38 g tri-sodium citrate) in 300 ml water. B: A placebo drink as in A containing 1 g red wine polyphenols, prepared as in Example 7, or C: a placebo drink as in A containing 1 g red wine polyphenol +30 mg quercetin (as prepared in Example 7). The trial commenced in the month of November and ended in December.

Blood samples were drawn into $K_3$ EDTA (1 mmol/L) 12 h after their supper meal before and after consuming the drinks for 4 weeks. Samples were centrifuged at 2000×g for 15 min at 4° C. to obtain plasma.

Total plasma antioxidant capacity was determined by the Ferric Reducing Ability of Plasma (FRAP) assay (Benzie and Strain, 1996 Analytical Biochem 239, 70–76) on fresh plasma. The estimation was carried out on the same day.

As shown in Table 5 there was a decrease of 10% in antioxidant capacity with the placebo drink, and a decrease of 1% with the red wine polyphenol powder, and an increase of 6% with the polyphenol powder with added quercetin.

It was concluded that supplementation of quercitin mixed with red wine polyphenols containing anthocyanin produced a greater increase in antioxidant capacity than the red wine polyphenols alone or a placebo drink. Moreover the beverage was fortified with a flavonol present in a water soluble form.

TABLE 5

Effect of administering a drink containing red wine polyphenols with or without quercetin to volunteers on then antioxidative capacity of plasma (FRAP)

| Treatment | FRAP[a] | | |
|---|---|---|---|
| | A<br>Placebo<br>(5)[b] | B<br>Red wine<br>Polyphenols<br>(4) | C<br>Red wine<br>polyphenols + quercetin<br>(4) |
| At start | 1221 ± 205 | 1277 ± 99 | 1151 ± 66 |
| After 4 weeks | 1148 ± 157 | 1260 ± 88 | 1215 ± 86 |
| Difference | −127 | 17 | 64* |

[a]mean ± SD
[b]no of subjects
*$P < 0.05$ (A vs. C)

What I claim is:

1. A method of increasing the solubility in water of a flavonol component of a flavonol-containing composition, the method comprising:
   providing a flavonol-containing composition;
   providing an anthocyanin-containing composition; and
   mixing the two compositions, said mixed composition having a greater concentration of anthocyanin over the concentration of flavonol.

2. A method according to claim 1, wherein said mixed composition is a nutritional supplement.

3. A method according to claim 1, wherein said composition has a mean molar ratio of anthocyanin to flavonol greater than 1:1.

4. A method according to claim 1, wherein the flavonol component comprises an aglycone or a glycoside.

5. A method according to claim 1, wherein the flavonol component comprises a flavonol selected from the group consisting of quercetin, kaempferol, myricetin and glycosides thereof.

6. A method according to claim 1, wherein the anthocyanin-containing composition comprises a fruit juice or vegetable extract.

7. A method according to claim 1, wherein the anthocyanin-containing composition is obtained from the group consisting of grapes, cranberries, blackberries, and blackcurrants.

8. A method according to claim 1, wherein the anthocyanin-containing composition is obtained from wine or dealcoholised wine.

9. A method according to claim 1, wherein the anthocyanin is selected from the group consisting of malvidin, cyanidin, delphinidin, paconidin, pelargonidin, polymeric anthocyanins, leucocyanidins, and glycosides thereof.

10. A method according to claim 1, wherein a flavonol-containing composition is added to and dissolved in an aqueous solution of anthocyanin.

11. A method according to claim 10, wherein the aqueous solution comprises dissolved anthocyanin at a concentration of at least 10 mg/L.

12. A method according to claim 10, wherein the aqueous solution comprises dissolved anthocyanin at a concentration of at least 50 mg/L.

13. A method according to claim 10, wherein the aqueous solution comprises dissolved anthocyanin at a concentration of at least 100 mg/L.

14. A method according to claim 10, wherein a mixture prepared by addition of a solid flavonol-containing composition to the aqueous solution of anthocyanin is heated above ambient temperature to assist in dissolution of the flavonol component, cooled, and any remaining undisolved flavonol removed by filtration and/or centrifugation.

15. A method according to claim 1, wherein a solid flavonol-containing composition is dissolved in ethanol or an ethanolic composition and added to an aqueous solution comprising anthocyanin.

16. A method according to claim 1, wherein a flavonol-containing composition is added to and dissolved in a wine or dealcoholised wine comprising an anthocyanin.

17. A method according to claim 1, wherein the flavonol-containing composition is added to and dissolved in a fruit juice or vegetable extract containing anthocyanin.

18. A method according to claim 1, wherein the flavonol-containing composition is mixed with a juice selected from the group consisting of grape, cranberry, blackberry, and blackcurrant.

19. A method of preparing a dry composition comprising a water-soluble flavonol component, the method comprising performance of the method of claim 10, and drying the resulting solution.

20. A method according to claim 19, performance of which produces a dry composition comprising at least 0.1% flavonol.

21. A method according to claim 19, performance of which produces a dry composition comprising at least 1% flavonol.

22. A method according to claim 19, performance of which produces a dry composition comprising at least 5% flavonol.

23. A method according to claim 19, performance of which produces a dry composition comprising at least 10% flavonol.

24. A method of providing a nutritional supplement with increased flavonol solubility, said nutritional supplement being an aqueous solution comprising dissolved flavonol at a concentration of 10 mg/L to 100 mg/L, the method comprising the steps of mixing, in any order, water, the flavonol and an anthocyanin, and forming an aqueous solution from the mixture, the solution comprising the flavonol dissolved at a concentration in excess of 10 mg/L, said flavonol concentration being less than the concentration of anthocyanin.

25. A method according to claim 24, wherein the solution comprises flavonol dissolved at a concentration in excess of 20 mg/L.

26. A method according to claim 24, wherein the solution comprises flavonol dissolved at a concentration in excess of 50 mg/L.

27. A method according to claim 24, wherein the solution comprises flavonol dissolved at a concentration in excess of 100 mg/L.

28. A method according to claim 24, wherein the aqueous solution is essentially ethanol-free.

* * * * *